(12) United States Patent
Wodnicki

(10) Patent No.: US 7,824,335 B2
(45) Date of Patent: Nov. 2, 2010

(54) RECONFIGURABLE ARRAY WITH MULTI-LEVEL TRANSMITTERS

(75) Inventor: Robert Gideon Wodnicki, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 548 days.

(21) Appl. No.: 11/796,002

(22) Filed: Apr. 26, 2007

(65) Prior Publication Data

US 2008/0264171 A1  Oct. 30, 2008

(51) Int. Cl.
*A61B 8/00* (2006.01)

(52) U.S. Cl. .................. 600/437; 600/447; 600/459

(58) Field of Classification Search ........... 73/625–628, 73/618, 620; 600/443–449, 453, 459
See application file for complete search history.

(56) References Cited

U.S. PATENT DOCUMENTS

| | | | | |
|---|---|---|---|---|
| 5,590,658 A | * | 1/1997 | Chiang et al. | 600/447 |
| 5,722,412 A | * | 3/1998 | Pflugrath et al. | 600/459 |
| 5,893,363 A | * | 4/1999 | Little et al. | 600/447 |
| 6,142,946 A | * | 11/2000 | Hwang et al. | 600/459 |
| 6,540,682 B1 | * | 4/2003 | Leavitt et al. | 600/447 |
| 6,836,159 B2 | | 12/2004 | Wodnicki | |
| 6,865,140 B2 | | 3/2005 | Thomenius et al. | |
| 2004/0254459 A1 | | 12/2004 | Kristoffersen et al. | |
| 2005/0096545 A1 | * | 5/2005 | Haider et al. | 600/447 |
| 2005/0169107 A1 | | 8/2005 | Thomenius et al. | |
| 2007/0016026 A1 | | 1/2007 | Thomenius et al. | |

* cited by examiner

*Primary Examiner*—Helen C. Kwok
(74) *Attorney, Agent, or Firm*—Scott J. Asmus

(57) ABSTRACT

An imaging probe having multi-level transmitter cells. The imaging probe includes a plurality of acoustical sub-elements for transmitting and receiving acoustic energy for imaging. Each of the multi-level transmitter cells is arranged along a respective transmitter cell path between a switching matrix and one of the acoustical sub-elements. The multi-level transmitter cells in the probe are capable of producing signals having multiple voltage levels.

33 Claims, 7 Drawing Sheets

RECONFIGURABLE ARRAY WITH MULTI-LEVEL TRANSMITTERS

STATEMENT REGARDING FEDERALLY SPONSORED RESEARCH AND DEVELOPMENT

The United States Government may have certain rights in this invention pursuant to U.S. Government Contract Number 1R01 EB002485-1 awarded by the National Institutes of Health.

CROSS-REFERENCE TO RELATED APPLICATIONS

This application is related to U.S. patent application Ser. No. 11/737,414 which was filed on Apr. 19, 2007, and is herein incorporated by reference.

BACKGROUND

The invention relates generally to ultrasound systems and more specifically to a reconfigurable array of multi-level transmitters. One specific application for such an array is in medical diagnostic ultrasound imaging systems. Another specific example is for non-destructive evaluation of materials, such as castings, forgings, or pipelines.

An ultrasound imaging system forms an image by acquiring individual ultrasound lines (or beams). The lines are adjacent to each other and cover the target area to be imaged. Each line is formed by transmitting an ultrasonic pulse in a particular spatial direction and receiving the reflected echoes from that direction. The spatial characteristics of the transmitted wave and the characteristics of the receive sensitivity determine the quality of the ultrasound image. It is desirable that the ultrasound line gathers target information only from the intended direction and ignores targets at other directions.

Conventional ultrasound imaging systems comprise an array of ultrasonic transducer elements that are used to transmit an ultrasound beam and then receive the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver may be dynamically focused at a succession of ranges along the scan line as the reflected ultrasonic waves are received.

For ultrasound imaging, the array typically has a multiplicity of transducer elements arranged in one or more rows and driven with separate voltages. By selecting the time delay (or phase) and amplitude of the applied voltages, the individual transducer elements in a given row can be controlled to produce ultrasonic waves that combine to form a net ultrasonic wave that travels along a preferred vector direction and is focused in a selected zone along the beam.

The same principles apply when the transducer probe is employed to receive the reflected sound in a receive mode. The voltages produced at the receiving transducer elements are summed so that the net signal is indicative of the ultrasound reflected from a single focal zone in the object. As with the transmission mode, this focused reception of the ultrasonic energy is achieved by imparting separate time delay (and/or phase shifts) and gains to the signal from each receiving transducer element. The time delays are adjusted with increasing depth of the returned signal to provide dynamic focusing on receive.

The quality or resolution of the image formed is partly a function of the number of transducer elements that respectively constitute the transmit and receive apertures of the transducer array. Accordingly, to achieve high image quality, a large number of transducer elements is desirable for both two- and three-dimensional imaging applications. The ultrasonic transducer elements are typically located in a hand-held transducer probe that is connected by a flexible cable to an electronics unit that processes the transducer signals and generates ultrasound images. The transducer probe may carry both ultrasound transmit circuitry and ultrasound receive circuitry.

Conventional medical ultrasound imaging creates two-dimensional, cross-sectional images using one-dimensional linear or phased array transducers. These transducers are built with approximately 100 to 200 elements arranged in a linear fashion. The transducer elements are connected to high-voltage transmitters or pulsers in the system. The transmitters or pulsers send waveforms to the transducer elements, which in turn convert the electrical waveforms into acoustic waves. By properly controlling the waveforms, a focused sound beam is generated. The signal level of the electrical waveforms can be several hundred volts in order to generate the desired level of acoustic energy. Connecting a few hundred transducer elements to the system is technically feasible with current technology. Current ultrasound systems address the problem of increased channel count by attempting to integrate discrete electronics at the board level. These systems typically are able to drive only about 128-256 channels and consume a large amount of power. Most of this power is expended to drive the cable.

Two-dimensional transducer arrays are required for electronically steered three-dimensional imaging. These types of transducer arrays typically employ several thousand elements. For proper beamforming, each one of these elements must be connected to a beamforming channel. Connecting several thousand elements to respective pulsers in the system is technically not feasible because a cable bundle of coaxial or other wire comprising a sufficient number of conductors for several thousand elements would be too thick and heavy to be ergonomically viable. Also, a cable that would connect the system pulsers to the transducer elements would present a very large capacitance load compared to the impedance of the two-dimensional array element. Therefore, a majority of the pulser current would be drawn into the cable capacitance while only a small fraction of the current would be drawn into the transducer element. As a result, only a small fraction of the energy supplied by the pulser would be converted to acoustic waves. Consequently, for a large array of tiny elements, much more power would have to be supplied by the pulser circuitry than would be required from a linear array. This additional power requirement might be tolerable for a full-size clinical ultrasound scanner. However, it would be prohibitive for a portable system, which would not be able to supply sufficient cooling for the pulsers. In addition, the portable system would suffer drastically reduced battery life.

U.S. patent application Ser. No. 10/697,518, filed on Oct. 30, 2003, discloses the concept of integrating pulsers or transmitters directly in the probe handle. This solves the problem of power consumption due to the cable, but does not address the more pragmatic concerns about the amount of power expended by the actual pulser control architecture. In addition, this patent application does not address the actual architecture of the pulser control circuit and does not treat the transmit/receive circuit.

Further, to provide accurate imaging, bipolar transmitters are often used to produce the ultrasound pulses in the system.

In contrast to unipolar transmitters, these transmitters typically generate waveforms defined by a sequence of square wave pulses of alternating negative and positive voltages. Advantageously, bipolar transmitters are inexpensive to make and easy to control, thereby making them a convenient choice over unipolar transmitters. However, bipolar transmitters provide a very limited voltage spectrum. In many systems, a larger number of voltage levels may be desirable to produce pulse sequences approximating signal waveforms, such as sinusoidal waveforms. Generating multiple voltage levels is generally expensive and difficult to implement. Further, transmitters capable of outputting numerous voltage levels are often inefficient and consume large amounts of power.

Accordingly, there is a need to solve the problem of driving a large number of small ultrasound transducers in a two-dimensional array configuration with minimal power expenditure and in a small footprint, wherein the transmitter is capable of producing multiple voltage levels.

Embodiments of the present invention may be directed to one or more of the challenges described above.

BRIEF DESCRIPTION

In accordance with one aspect of the present technique, there is provided a probe. The probe comprises a plurality of acoustical sub-elements and a plurality of multi-level transmitter cells, wherein each of the multi-level transmitter cells is coupled to a respective acoustical sub-element. Each of the plurality of multi-level transmitter cells comprises a waveform decoder configured to decode an input waveform. Each of the plurality of multi-level transmitter cells further comprises a transmitter controller configured to receive a decoded output from the waveform decoder. Each of the plurality of multi-level transmitter cells further comprises an output stage configured to receive an output from the transmitter controller and further configured to transmit a waveform to a respective one of the plurality of acoustical sub-elements.

In accordance with another aspect of the present technique, there is provided an imaging system. The imaging system comprises imaging electronics and a probe coupled to the imaging electronics through a plurality of conductive channels. The probe comprises a switching matrix configured to receive waveform information on each of the plurality of conductive channels and to transmit the waveform information along a plurality of transmit cell paths. The probe further comprises a respective multi-level transmitter cell arranged along each of the plurality of transmit cell paths and comprising each of a waveform decoder, a transmitter controller and an output stage, wherein the multi-level transmitter cell is configured to produce a signal having at least two voltage levels.

In accordance with another aspect of the present technique, there is provided a method of operating an imaging probe. The method comprises transmitting one or more signals to the imaging probe. The method further comprises decoding each of the one or more signals in a respective transmitter cell arranged along each of a plurality of transmitter cell paths. The method further comprises producing a multi-level voltage signal from each of the respective transmitter cells. The method further comprises operating a respective transducer utilizing a respective multi-level voltage signal.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
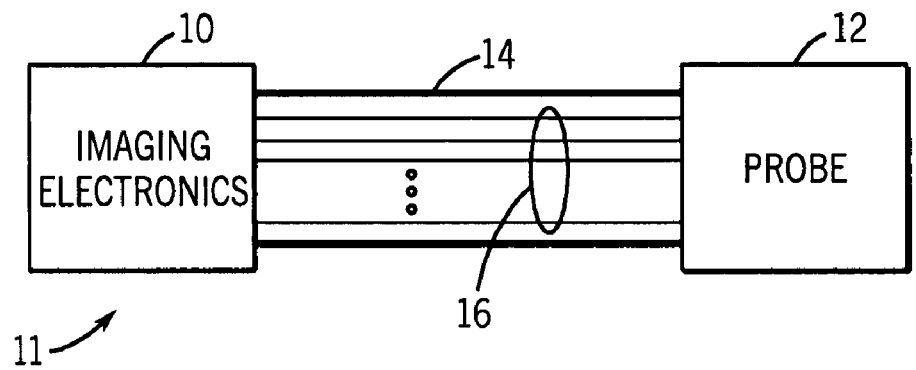
FIG. 1 is a block diagram of an imaging system in accordance with embodiments of the present invention.

FIG. 1 illustrates a block diagram of an imaging system 11 formed in accordance with an embodiment of the present invention. The imaging system 11 may comprise an ultrasound system, for instance. As will be appreciated, the imaging system typically includes imaging electronics 10 and a probe 12. The imaging electronics 10 and the probe 12 will be described further below with regard to FIG. 5. In accordance with embodiments of the present invention, the probe 12 includes an array of multi-level transmitter cells, each capable of producing multiple voltage levels for transmission to a respective transducer element. The imaging electronics 10 and probe 12 are generally coupled together via one or more cables 14. Each cable includes a number of electrical conductors 16, wherein each of the electrical conductors 16 corresponds to a unique channel. Alternately, a cable may not be present as would be the case for a fully portable hand-held system.

In general, and as will be described and illustrated further below with respect to FIGS. 5-9, the imaging system 11 includes multilevel transmitters which drive transducers within the probe 12 to emit pulsed ultrasonic signals into a body. A variety of geometries may be used. The ultrasonic signals are back-scattered from structures in the body, like blood cells or muscular tissue, to produce echoes which return to the transducers. The echoes are received by a receiver and passed through a beamformer, which performs beamforming and outputs an RF signal. The RF signal may then be processed or demodulated to form IQ data pairs representative of the echo signals.

For an ultrasound system, the imaging system 11 may also include one or more signal processors to process the acquired ultrasound information (i.e., RF signal data or IQ data pairs) and prepare frames of ultrasound information for display. The signal processor is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored during a scanning session and processed in less than real-time.

Figure 2:
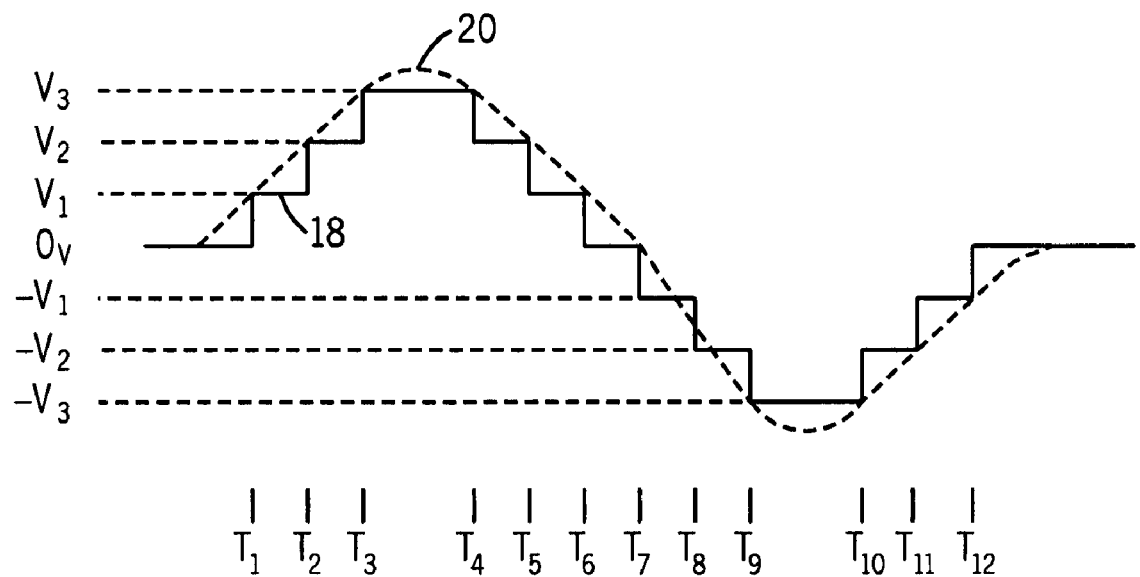
FIGS. 2-4 are timing diagrams illustrating exemplary signals that may be produced in accordance with embodiments of the present invention.
Figure 3:
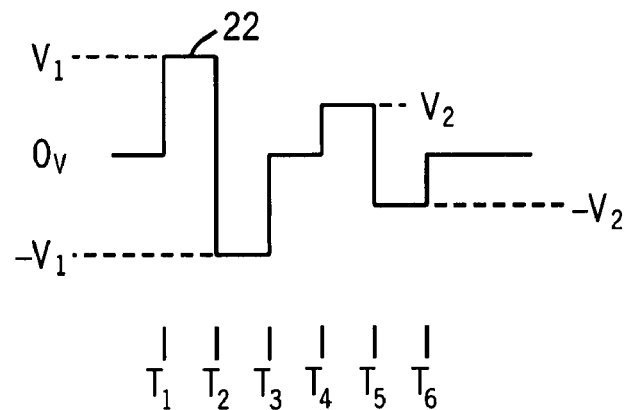
Figure 4:
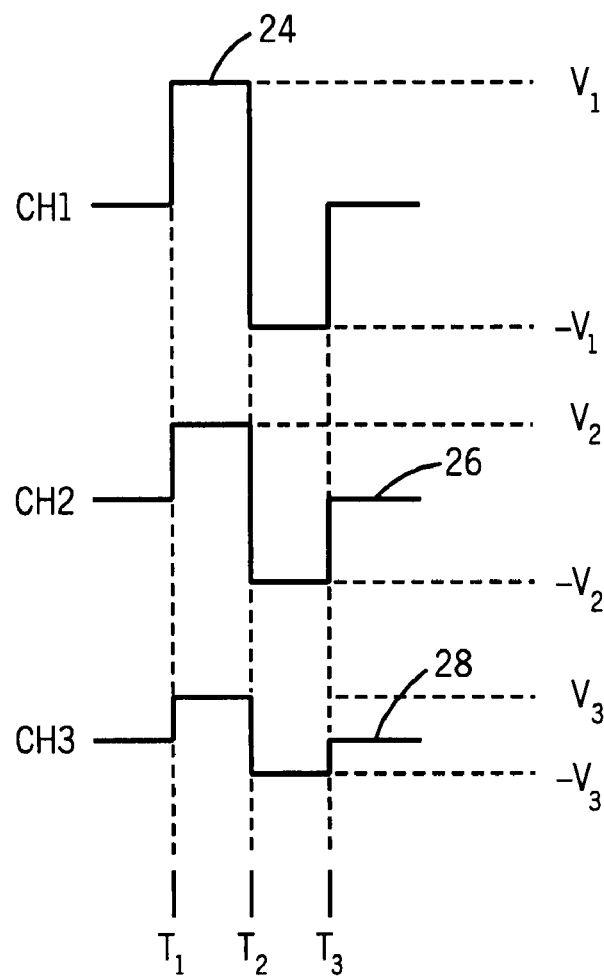

While uni-level signals and bi-level signals may be used for sensing in an ultrasound system, multi-level signals are often desirable. For example, FIGS. 2-4 illustrate various output waveforms that may be desirable in an ultrasound system and which may be formed employing the multi-level transmitters described herein. More specifically, FIG. 2 illustrates a waveform 18 having various discreet voltage levels $V_1, V_2, V_3$, 0V, $-V_1, -V_2$, and $-V_3$, for example, at various times $T_1$-$T_{12}$. Any number of voltage levels may be produced, depending on the capability of the multi-level transmitter that produces it. As illustrated, if the multi-level transmitter is capable of producing a sufficient number of voltage levels, the waveform 18 may closely approximate an ideal sinusoidal waveform 20. Other useful waveforms may, for example, take the form of a Gaussian shaped pulse of 1.5 or more periods in duration, and/or coded pulses for improved signal penetration into the body.

In some instances it may be desirable to be able to transmit multiple successive pulses on the same channel where each pulse has a different peak-to-peak voltage, as illustrated by the waveform 22 of FIG. 3. These waveforms can be generated using the methods described herein by encoding different transmit voltages on multiple timing cycles. For instance, in each cell there could be the voltage selector circuit, as will be described and illustrate with regard to FIG. 9, which could be used to choose between five globally distributed control voltages, each of which would cause the circuit to output one of the required voltages 0V, $+/-V_1$ or $+/-V_2$. As will be understood through the description of FIG. 9, the requirements for this circuit are significantly less than that for having a local DAC followed by a high voltage amplifier in every multi-level transmitter cell, and the amount of information to communicate is also greatly reduced. This will be advantageous in accordance with the embodiments described herein, wherein the multi-level transmitters are located in the space-confining probe 12, as discussed further below.

In other applications, it may be advantageous to be able to transmit similar waveforms on different channels where each channel has a unique peak-to-peak output voltage, as illustrated in FIG. 4. As illustrated, the waveform 24 on channel 1 (CH1) has a peak-to-peak voltage of $2*V_1$. The waveform 26 on channel 2 (CH2) has a peak-to-peak voltage of $2*V_2$. The waveform 26 on channel 3 (CH3) has a peak-to-peak voltage of $2*V_3$, where $V_1, V_2$ and $V_3$ are different voltages. As with the multi-level waveforms illustrated in FIGS. 2 and 3, these waveforms can again be generated using any of the methods described herein. Further, as will be appreciated, various other multi-level waveforms may be desirable and may also be generated employing the techniques and embodiments described herein. The waveforms of FIGS. 2-4 are simply given by way of example to illustrate a few of the possible applications of multi-level transmitters in accordance with embodiments of the present invention.

Figure 5:
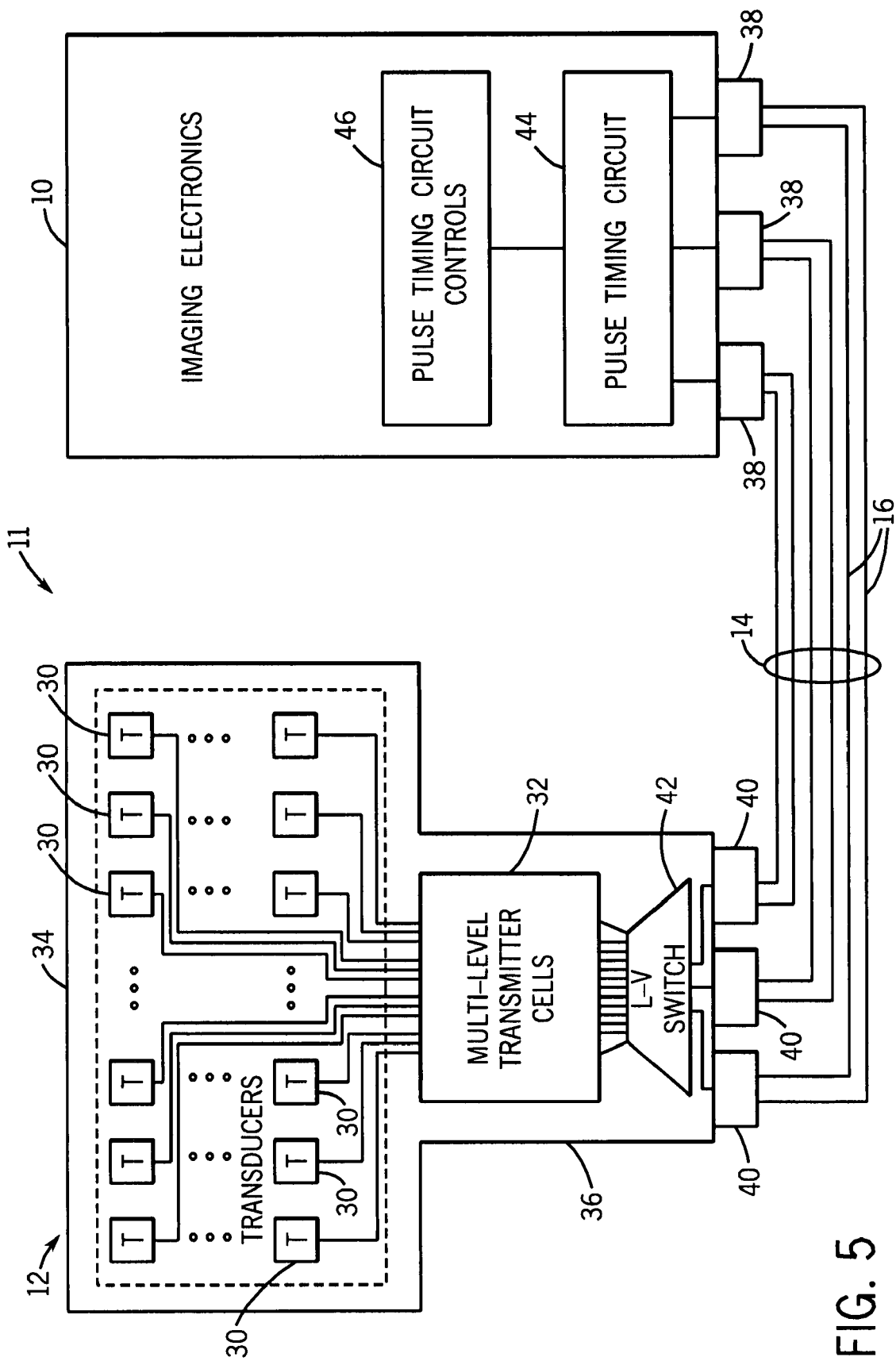
FIG. 5 is block diagram illustrating a more detailed view of the imaging system of FIG. 1, in accordance with embodiments of the present invention.

Turning now to FIG. 5, an exemplary imaging system 11, in accordance with embodiments of the present invention, is illustrated. For simplicity, conventional components and circuitry in the imaging system 11 for processing the data to generate an image have been omitted. In accordance with one embodiment of the present invention shown in FIG. 5, the ultrasonic probe 12 comprises a number of acoustical sub-elements 30 and a corresponding number of high-voltage multi-level transmitter cells 32. The acoustical sub-elements 30 may comprise a capacitive micromachined ultrasonic transducer (cMUT), a polyvinylidene flouride (PVDF) sensor, a Cadmium Zinc Telluride (CZT) sensor, a piezoelectric transducer (PZT), or a piezoelectric micro machined ultrasonic transducer (PMUT), for instance. Various exemplary embodiments of the multi-level transmitter cells 32 will be described further with reference to FIGS. 6-9. In one embodiment, there is one multi-level transmitter cell 32 for each acoustical sub-element 30. In accordance with embodiments of the present invention, the acoustical sub-elements 30 are disposed in the probe head 34 and the multi-level transmitter cells 32 are disposed in the probe handle 36, as illustrated. As previously described, the probe 12 is electrically coupled to the ultrasound imaging electronics 10 by one or more cables 14 comprising a multiplicity of electrical conductors 16. Each cable 14 is coupled to the imaging electronics 10 and to the probe 12 by respective cable connectors 38 and 40. The multi-level transmitter cells 32 receive pulse timing signals via a low-voltage switching matrix 42 which is also incorporated in the probe handle 36.

Placing the multi-level transmitter cells 32 in the probe handle 36 advantageously permits pulse timing circuitry 44 (controlled by pulse timing control circuitry 46) to be located either in the imaging electronics 10, as shown in FIG. 5, or in the probe handle (not shown). During the transmit phase, each acoustical sub-element 30 receives a pulse train from a respective multi-level transmitter cell 32. Parameters of the respective pulse train in each channel are varied to achieve focused ultrasound beam transmission. For instance, the multi-level transmitter cells 32 in the probe handle 36 may be configured to produce one or more of the exemplary multi-level waveforms illustrated in FIGS. 2-4. The pulse timing circuit 46 generates multiple low-voltage transmit control (i.e., timing) signals that are carried by the coaxial cables 14 from the imaging electronics 10 to the probe 12. When the timing signals reach probe handle 36, they are routed to individual multi-level transmitter cells 32 via the low-voltage switching matrix 42, which is reprogrammed before each transmit operation. Routing of signals is such that all acoustical sub-elements 30 that are part of a given transmit element are connected together to receive the same low-voltage transmit control signal. Similarly all sub-elements 30 that are part of a given receive element are connected together such that their receive signals contribute to the net receive signal for that element.

In accordance with embodiments disclosed herein, there is a one-to-one correspondence of high-voltage multi-level transmitter cells 32 to acoustical sub-elements 30. The low-voltage transmit control signals are routed through the low voltage switching matrix 42. Once the low-voltage transmit control signals reach an individual cell 32, they are decoded and used to control the local multi-level transmitters or output stage of the multi-level transmitter cells 32 to drive individual acoustical sub-elements 30, as described further below with respect to FIG. 6.

Figure 6:
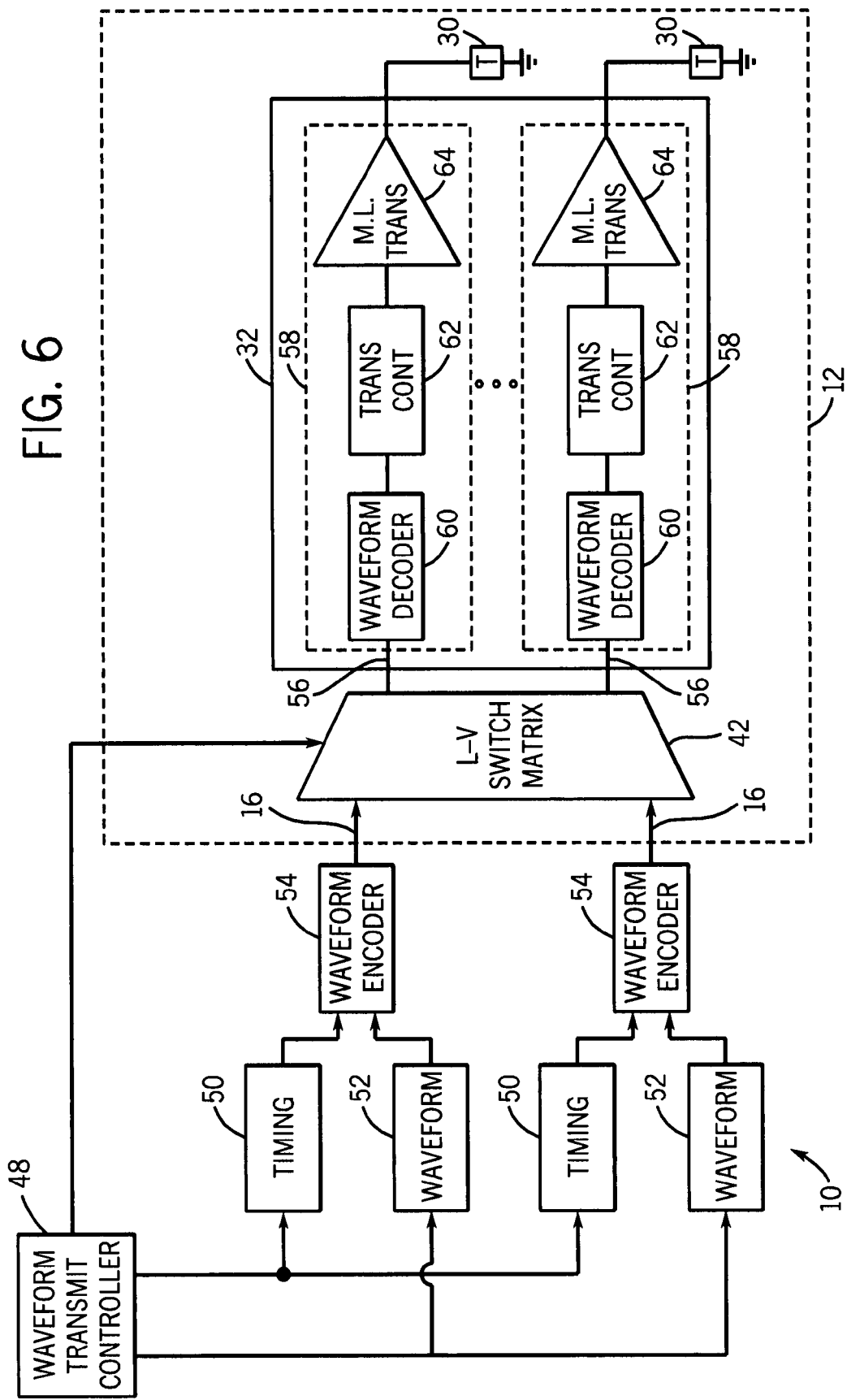
FIG. 6 is a more detailed view of the imaging system of FIG. 5, illustrating the multi-level transmitter cells in accordance with embodiments of the present invention.

Turning now to FIG. 6, the architecture for a multi-level reconfigurable array in accordance with embodiments of the present invention is illustrated. Generally, the multi-level reconfigurable array architecture includes components which generate encoded waveform descriptions which are communicated through the switching matrix 42 in the probe 12, to the multi-level transmitter cells 32. More specifically, a waveform transmit controller 48 in the imaging electronics 10 generates control information including timing information 50 and waveform information 52. The timing information 50 indicates when the waveform transmitter or pulser should pulse. The waveform information 52 indicates the shape of the waveform to be produced by indicating at which voltage or current levels the pulses should be transmitted. The control information for each electronic conductor or channel 16 is then encoded by a respective waveform encoder 54 on each channel such that it can be communicated more efficiently to the switching matrix 42. While only two channels 16 are illustrated, as previously described, any number of channels 16 (i.e., 1-k channels) may be provided.

Once the information for each channel 16 is encoded by a respective waveform encoder 54, it is routed through the low voltage switching matrix 42 in the probe 12. The switching matrix 42 is used to select groups of multi-level transmit cells, collectively indicated by the reference numeral 32 and individually indicated by the reference numeral 58. Each respective multi-level transmit cell 58 has a unique transmit cell path 56 which is coupled between the switching matrix 42 and a respective acoustical sub-element 30, such as a transducer. As will be appreciated, there any desirable number of transmit cells 58 may be employed (i.e., 1-N transmit cells). Each group of transmit cells 58 receives the same waveform shape 52 and timing 50 information simultaneously.

After it leaves the switching matrix 42, the control signals are transmitted to the individual multi-level transmitter cells 58. In accordance with embodiments of the present invention, each multi-level transmitter cell 58 includes a waveform decoder 60, a transmitter controller 62 and a multi-level transmitter or output stage 64. The waveform decoder 60 unwraps the packaged information about timing and waveform shape and uses it to feed into the transmitter controller 62. The transmitter controller 62 generates the control voltages to actuate the transmitter or output stage 64. The transmitter 64 then drives the acoustical element 30, here a transducer, with the required multi-level waveform.

As will be appreciated, various embodiments of the waveform decoder 60, transmitter controller 62 and output stage 64 may be employed, in accordance with embodiments of the invention. Details of various embodiments of the waveform decoder 60, transmitter controller 62 and output stage 64, and the operation thereof will be discussed further below. However, before a detailed discussion of various encoding/decoding schemes (waveform decoder 60), transmitter controller 62 and output stage 64, exemplary embodiments of the multi-level transmitter cell 58 will be illustrated with reference to FIGS. 7-9, and generally described.

Figure 7:
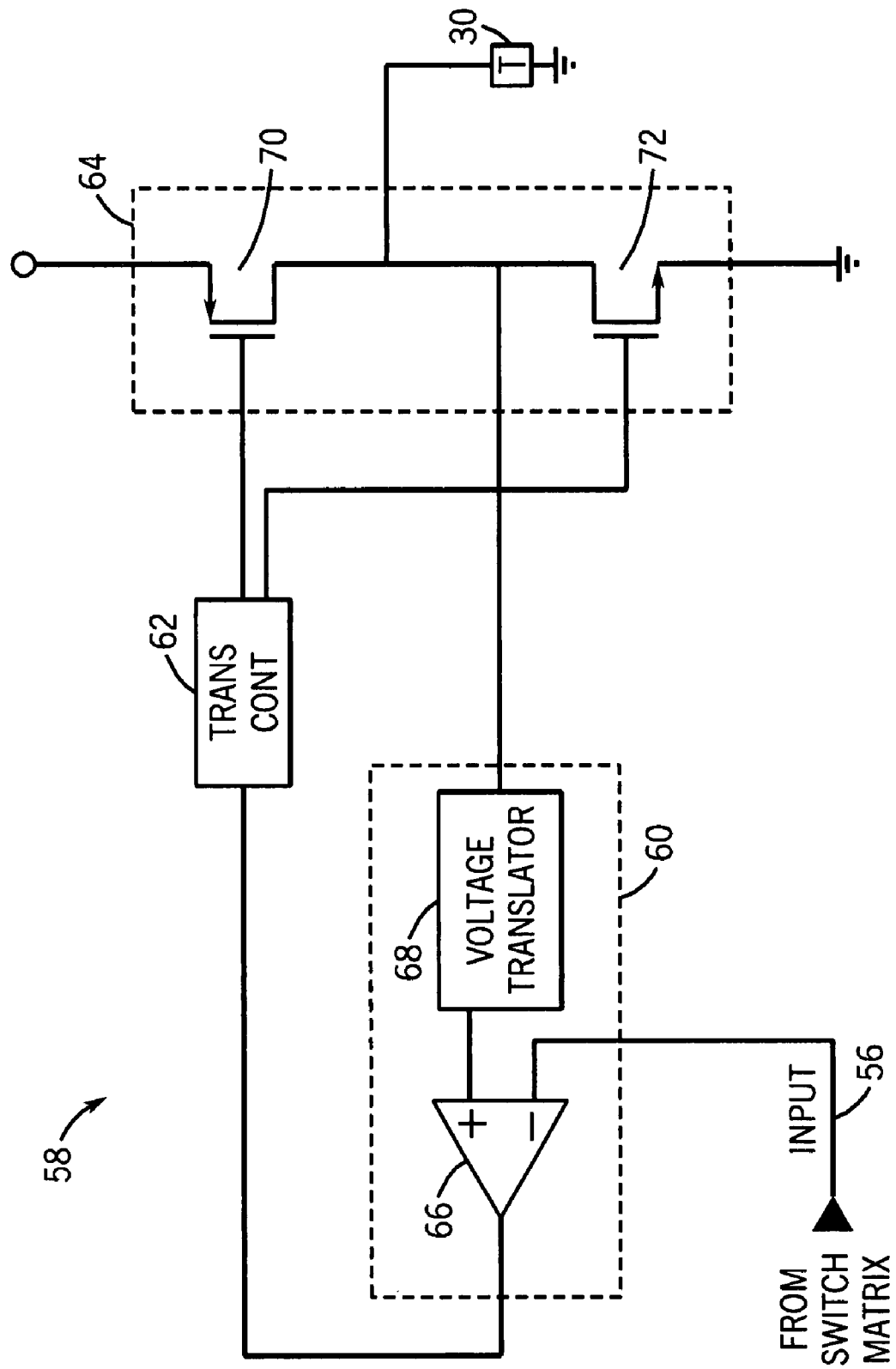
FIGS. 7-9 illustrate partial schematic diagrams for various embodiments of the multi-level transmitter cells in accordance with exemplary embodiments of the present invention.

Referring initially to FIG. 7, a first embodiment of the multi-level transmitter cell 58 includes a waveform decoder 60 comprising a comparator 66 and a voltage translator 68. In this embodiment, the comparator 66 acts as a decoder. Further, the output stage 64 includes each of a PMOS and NMOS transistor 70 and 72, respectively, coupled in series between a voltage source and ground. As will be appreciated, while ground is used as a reference, it will be understood that this reference could be replaced by a negative supply equal to or a different value from the positive supply, without altering the functionality of the circuit. The transmitter controller 62 acts like a set point controller such that the output voltage is compared to the input control voltage and any error is used to drive the output to match the control voltage, as will be appreciated by those skilled in the art. It will further be appreciated that the output drive devices are shut off once the desired voltage is reached and are thus not statically biased which will conserve a considerable amount of power when compared to conventional multi-level pulser circuits.

Figure 8:
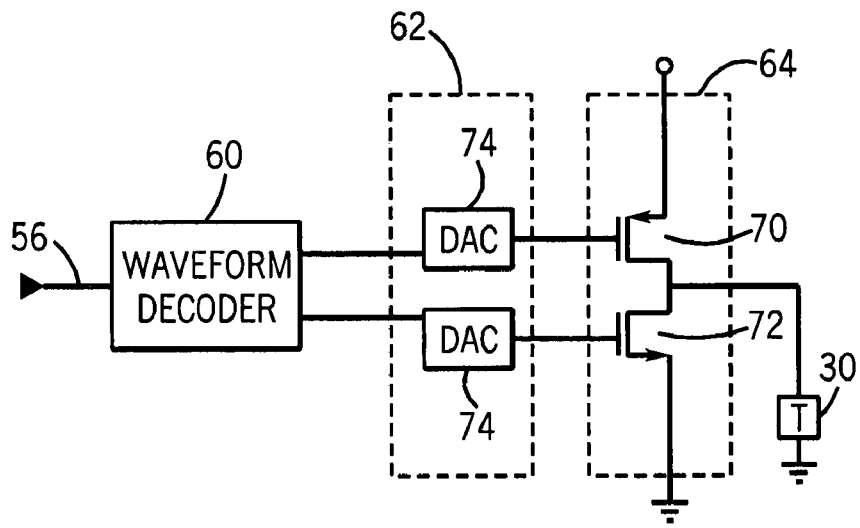

FIG. 8 illustrates a second embodiment of the multi-level transmitter cell 58. Rather than providing a feedback loop from the output stage 64 to the waveform decoder 60, digital to analog converters (DACs) 74 are employed as the transmitter controller 62 to control the output stage 64 and transmission to the acoustical sub-element 30.

Figure 9:
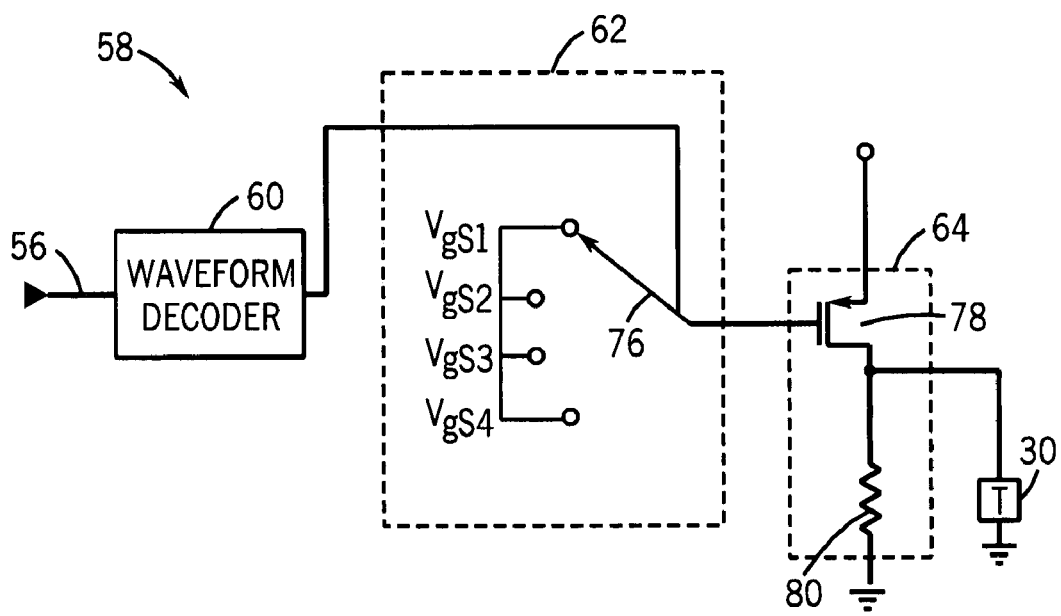

FIG. 9 illustrates a third embodiment of the multi-level transmitter cell 58. In the embodiment illustrated in FIG. 9, the transmitter controller 62 comprises a switch 76 to allow for switching between four gate voltages $V_{gs1}$-$V_{gs4}$ relative to the high voltage source voltage HVP, depending on the input control waveform. In one embodiment, $V_{gs1}$=HVP-0V, $V_{gs2}$=HVP -1.0V, $V_{gs3}$=HVP-2.5V and $V_{gs4}$=HVP-5V, for example. The gate voltage is applied to a resistor loaded output stage 64 comprising a transistor 78 and a resistor 80. The gate of the transistor 78 is controlled by the gate voltage $V_{gs1}$. Here the transistor 78 is a high voltage field effect transistor which is used to modulate a current that is fed into the resistor 80. The output voltage across the transducer 30 is that developed across the resistor 80 due to the drive current. Advantageously, an output stage 64, in accordance with this exemplary embodiment may be implemented in a very compact area and will draw a non-negligible current during the transmit phase but can be switched off during the receive phase.

The embodiments illustrated in FIGS. 6-9 will be better understood with further discussion of various techniques and embodiments that may be employed with regard to the waveform decoder 60, transmitter controller 62 and output stage 64. Referring initially to the encoding/decoding of the waveform data (i.e., the encoder 54 and decoder 60), various techniques may be employed. For instance, pulse width modulation (PWM) may be employed to encode/decode the waveforms. In this embodiment, the width of a control pulse may represent the amount of current to be sourced by the output stage 64 at a given time step.

Alternatively, encoding/decoding may be facilitated using an analog voltage or current waveform. For example, the voltage level in the encoded signal is input directly to the gates of the transmit output devices or via a level shifting and gain network, and used to directly modulate the output current by changing the gate-source voltage of these devices. The analog voltage may be a linear description of the output waveform, or it may be pre-warped to account for the non-linear Ids/Vgs characteristic of the output devices.

In another exemplary embodiment, digital data may be employed for waveform encoding/decoding. For example, multiple digital data bits can be transmitted simultaneously for each channel 16. When these bits arrive at the respective multi-level transmitter cell 58, they are decoded at the waveform decoder 60 and used to select among a group of voltage levels to control the output stage 64. Digital data can be transmitted in any suitable format, including, but not limited to serial format, parallel format, or multiple bipolar waveforms, wherein each waveform encodes for one of the bits controlling the output signal, and the positive pulse encodes for the positive output while the negative encodes for the negative output.

In another exemplary embodiment, decoupled data transmission may be employed for waveform encoding/decoding. Here the timing and level information are transmitted separately, as previously described with reference to FIG. 6. The information may be sent simultaneously, at different times, or parametrically. For example, if the timing and waveform information is sent simultaneously, a timing signal is transmitted on a different signal line from the waveform shape information. (See e.g., FIG. 6). If the information is sent at different times, the waveform shape information is programmed ahead of time in each transmitter cell 58 and then triggered by subsequent timing signals. If the information is sent parametrically, control parameters are propagated separately from the general waveform control information and used to shape the waveform in real time during imaging. Further, as will be appreciated, a combination of any of these encoding/decoding techniques may be employed in accordance with embodiments of the invention.

Referring now to various embodiments of the transmitter controller 62, the transmitter controller 62 may comprise a set point controller, where the output voltage is compared to the input control voltage and any error is used to drive the output to match the control voltage, as illustrated in FIG. 7. In another embodiment, a locally implemented DAC can be used in each transmitter cell 58 to convert the digital control signals to analog control voltages which can be used to drive the output stage, as illustrated in FIG. 8. Alternatively, the transmitter controller 62 may comprise a switch to locally select a control voltage, as illustrated in FIG. 9. As previously described, the input control voltage is decoded to select from a number of voltage levels locally in each multi-level transmitter cell 58 to control the output stage 64. These voltages are optimally generated globally for the entire transmitter matrix in order to improve signal to noise ratio and uniformity. As the control voltage propagates through the switching matrix 42, its waveform shape is corrupted due to the transfer function of the switches themselves. In decoding this imperfect waveform and using it to select among a number of ideal voltage sources, a high quality output waveform can be realized. In another embodiment, a level shifter may be employed. In this embodiment, the control signal is used to directly drive the control terminals of the transmitter output devices in the output stage 64. In this case it may be necessary to translate the control signal such that it is able to drive high-side and low-side high voltage devices.

Referring now to the output stage 64, the output stage may comprise an analog buffer/amplifier. In accordance with this embodiment, the control signal is amplified or buffered by the output stage 64 such that it can drive the transducers 30. This is the most versatile output stage 64 but it may suffer from control signal deformation due to the switch transfer function as well as high power consumption due to use of statically biased output drivers. To conserve power, it may be desirable to switch the drivers off during the receive phase.

In another exemplary embodiment, a DAC may be employed. A local high voltage DAC can be used to convert a digitally encoded control signal to a high voltage output. It is also possible to use a low voltage DAC followed by a high voltage amplifier. This technique will be area intensive and also power intensive but will yield the most accurate representation of the output waveform.

Alternatively, as illustrated in FIG. 9, a resistor loaded output stage 64 may be employed. As previously described, a single high voltage output FET 78 is used to modulate a current that is fed into a resistor 80. The output voltage across the transducer 30 is the same as the voltage produced across the resistor 80 due to the drive current. This circuit can be implemented in a very compact area. It will draw a non-negligible current during the transmit phase but can be switched off on receive.

Alternatively, a time-ratioed output stage 64 may be employed. In accordance with this embodiment, the control input signals to the output stage 64 are ratioed such that the output only generates drive current for a short period of time (e.g., 5-10 nanoseconds). During this short time period, the output stage 64 charges the load capacitance produced by the transducer 30. Because the load is mostly capacitive (e.g., 90% or more), the output voltage rises approximately linearly with time as long as a constant current is present. When the constant current is switched off, the output remains at the final value. Since the current is kept constant, the final output voltage can be set by appropriately setting the amount of time that the driver remains on. Although this time period is short, it can be generated locally using an inverter chain, wherein the propagation delays of the individual inverters can be used to establish the desired delay.

Figure 10:
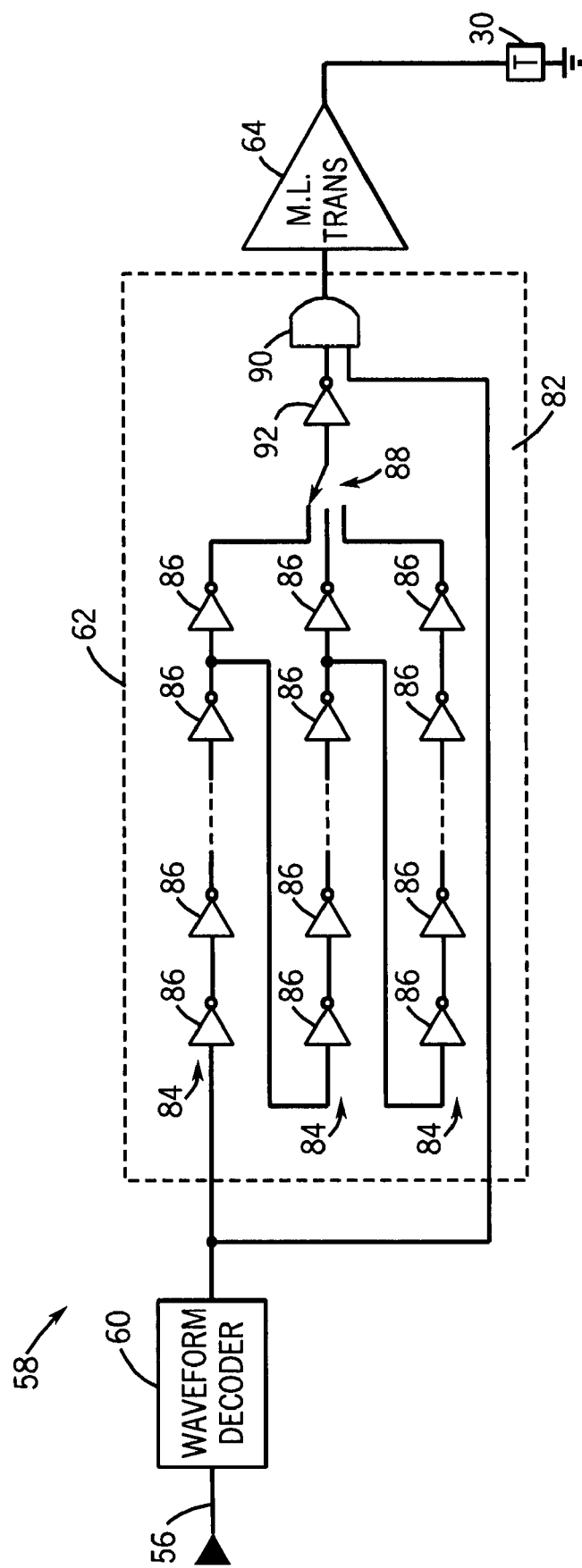
FIG. 10 illustrates an exemplary transmitter controller that may be employed in a multi-level transmitter cell in accordance with embodiments of the present invention.

For example, FIG. 10 illustrates an exemplary transmitter controller 62 comprising a control signal generation circuit 82 including chains 84 of individual inverters 86 which may be employed to generate multiple output levels which may be delivered to an output stage 64. In the presently illustrated embodiment, the circuit 82 includes three chains 84. Each chain 84 produces a respective delay output (DELAY 1, DELAY 2 and DELAY 3). A switch 88 is used to select among the delay outputs (DELAY 1, DELAY 2 or DELAY 3), depending on the required transmission level. A logical AND gate 90 may be used to combine the signal produced by the waveform decoder 60 with the inverse of a selected delay output (DELAY 1, DELAY 2 and DELAY 3), which may be produced using an inverter 92, to produce the output signal (OUTPUT) used to control the output stage 64. The output of this type of transmitter controller 62 is high only when both the input and the selected delayed output are high at the same time. This causes the output current to remain on for a very short and predetermined period of time which can be accurately controlled since the propagation delay is a well known design parameter. As illustrated in FIG. 10, the length of time that the output current is driven can be increased in ratioed increments by adding more inverters.

In the circuit 82, the amount of delay in the output signal (OUTPUT) from the transmitter controller 62 may be selected by controlling the switch 88 to select a delay output (DELAY 1, DELAY 2 and DELAY 3) depending on whether a short delay is desired (DELAY 1), a longer delay is desired (DELAY 2) or an even longer delay (DELAY 3) is desired. When the output signal (OUTPUT) is used to turn on a pulser, these three signals could be used to select among low, medium and high output level pulse outputs. The same principle may be extended to as many increments in control delay as are required to provide very fine quantization of the output signal under digital control. While the pulse control can be generated locally for every transmitter, it may also be possible to generate a global signal on the same chip as the transmitter array, outside of the transmitter matrix. This signal could then be directed through a low voltage switch matrix and delivered to those transmitters that require it. As will be appreciated, however, the high frequency edges of the very short pulses may be easier to generate and transmit on-chip, rather than being generated by an off-chip device.

In another exemplary embodiment, a current-ratioed output stage may be employed. This output stage 64 is similar to the time-ratioed output stage, but here the time period is kept constant, while the output current is controlled by the input waveform. The time period can be determined using the same circuits described for the time-ratioed approach but with only a single hard-wired delay group. Therefore, by $dV=1*dT/C$, the output voltage is developed across the transducer capacitance (C) depending on the amount of current (I) that is sourced by the transmitter output devices. As with the time-rationed transmitter, the output voltage waveform is built up using a series of controlled transitions from one step to the next, as in the output stage of FIG. 7. Advantageously, the time-rationed and current-rationed output stages 64 can be made very small and consume minimal power since current is only sourced to move the output voltage from one step to the next. It is also possible to combine the time-rationed and current rationed output stages into a single transmitter output stage which can be controlled either by controlling the output current or controlling the amount of time allowed for each output current step. Complete flexibility in this regard may be provided by the circuit illustrated in FIG. 8.

While only certain features of the invention have been illustrated and described herein, many modification and changes will occur to those skilled in the art. It is, therefore, to be understood that the appended claims are intended to cover all such modifications and changes that fall within the true spirit of the invention.

The invention claimed is:

1. A probe comprising:
    a plurality of acoustical sub-elements; and
    a plurality of multi-level transmitter cells, wherein each of the multi-level transmitter cells is coupled to a respective acoustical sub-element, and wherein each of the plurality of multi-level transmitter cells is capable of producing multiple voltage levels for transmission to said respective acoustical sub-element and said multi-level transmitter cells comprises:
        a waveform decoder configured to decode an input analog waveform;
        a transmitter controller configured to receive a decoded output from the waveform decoder; and
        an output stage configured to receive an output from the transmitter controller and further configured to transmit a waveform to a respective one of the plurality of acoustical sub-elements.

2. The probe, as set forth in claim 1, wherein each of the plurality of acoustical sub-elements comprises one of a capacitive micromachined ultrasonic transducer (cMUT), a polyvinylidene fluoride (PVDF) sensor, a Cadmium Zinc Telluride (CZT) sensor, a piezoelectric transducer (PZT), or a piezoelectric micro machined ultrasonic transducer (PMUT).

3. The probe, as set forth in claim 1, wherein each of the plurality of multi-level transmitter cells comprises a transmit path configured to electrically couple the respective waveform decoder, transmitter controller and output stage along the path.

4. The probe, as set forth in claim 1, wherein the waveform decoder comprises a voltage translator configured to receive an input signal from the output stage and further comprising a comparator configured to receive an output signal from the voltage translator and the input waveform.

5. The probe, as set forth in claim 1, wherein the transmitter controller comprises a plurality of digital-to-analog converters.

6. The probe, as set forth in claim 1, wherein the transmitter controller comprises a switch configured to couple the output stage to any one of a plurality of voltage sources.

7. The probe, as set forth in claim 1, wherein the transmitter controller comprises a set point controller or a level shifter.

8. The probe, as set forth in claim 1, wherein the transmitter controller comprises a circuit which turns on the output stage for a predetermined and unvarying short period of time during which a variable current is caused to flow to the output stage in proportion to the decoded output of the waveform decoder.

9. The probe, as set forth in claim 1, wherein the transmitter controller comprises a circuit which turns on the output stage causing a predetermined and fixed current to flow to the output stage for a short and variable period of time which is in proportion to the decoded output of the waveform decoder.

10. The probe, as set forth in claim 1, wherein the transmitter controller comprises a circuit which turns on the output stage causing a varying current proportional to a first aspect of the decoded output of the waveform decoder to flow for a short and variable period of time, which is in proportion to a second aspect of the decoded output of the waveform decoder.

11. The probe, as set forth in claim 1, wherein the output stage comprises a first transistor coupled in series with a second transistor, wherein the series connection between the first and second transistors is coupled to the respective one of the plurality of acoustical sub-elements.

12. The probe, as set forth in claim 1, wherein the output stage comprises a transistor coupled in series with a resistor, wherein the series connection between the transistor and the resistor is coupled to the respective one of the plurality of acoustical sub-elements.

13. The probe, as set forth in claim 1, further comprising a low voltage switching matrix configured to receive timing and waveform information and further configured to transmit the information to each of the plurality of waveform decoders.

14. The probe, as set forth in claim 1, wherein each of the plurality of acoustical sub-elements is responsive to a dedicated one of the plurality of multi-level transmitter cells.

15. The probe, as set forth in claim 1, comprising a probe head and a probe handle, wherein each of the plurality of acoustical sub-elements is located in the probe head and wherein each of the plurality of multi-level transmitter cells is located in the probe handle.

16. The probe, as set forth in claim 1, comprising a probe head and a probe handle, wherein each of the plurality of acoustical sub-elements is located in the probe head and wherein each of the plurality of multi-level transmitter cells is also located in the probe head, directly adjacent to the acoustical sub-elements.

17. An imaging system comprising:
    imaging electronics generating analog waveform information; and
    a probe coupled to the imaging electronics through a plurality of conductive channels, wherein the probe comprises:
        a switching matrix configured to receive said analog waveform information on each of the plurality of conductive channels and to transmit the waveform information along a plurality of transmit cell paths; and
        a respective multi-level transmitter cell arranged along each of the plurality of transmit cell paths and comprising each of a waveform decoder, a transmitter controller and an output stage, wherein the multi-level transmitter cell is configured to produce a signal having at least two voltage levels.

18. The imaging system, as set forth in claim 17, comprising an ultrasound imaging system.

19. The imaging system, as set forth in claim 17, wherein the plurality of conductive channels are arranged in a cable.

20. The imaging system, as set forth in claim 17, wherein the imaging electronics comprise pulse timing circuit controls and a pulse timing circuit.

21. The imaging system, as set forth in claim 17, wherein the imaging electronics comprises waveform shape controls and a waveform shape encoding circuit.

22. The imaging system, as set forth in claim 17, wherein the switching matrix comprises a low voltage switching matrix.

23. The imaging system, as set forth in claim 17, further comprising a plurality of acoustical sub-elements arranged in the probe and wherein each of the plurality of acoustical sub-elements is configured to receive the signal from a respective one of the multi-level transmitter cells.

24. The imaging system, as set forth in claim 23, wherein each of the plurality of acoustical sub-elements comprises one of a capacitive micromachined ultrasonic transducer (cMUT), a polyvinylidene fluoride (PVDF) sensor, a Cadmium Zinc Telluride (CZT) sensor, a piezoelectric transducer (PZT), or a piezoelectric micro machined ultrasonic transducer (PMUT).

25. A method of operating an imaging probe comprising:
    transmitting one or more analog signals to the imaging probe;

decoding each of the one or more analog signals in a respective transmitter cell arranged along each of a plurality of transmitter cell paths;
producing a multi-level voltage signal from each of the respective transmitter cells; and
operating a respective transducer utilizing a respective multi-level voltage signal.

26. The method, as set forth in claim 25, wherein transmitting one or more signals comprises transmitting one or more timing and waveform signals to the imaging probe.

27. The method, as set forth in claim 25, wherein transmitting one or more signals comprises transmitting one or more signals from imaging electronics located externally with respect to the imaging probe.

28. The method, as set forth in claim 25, wherein transmitting one or more signals comprises transmitting one or more signals from imaging electronics located within the imaging probe.

29. The method, as set forth in claim 25, wherein producing a multi-level voltage signal comprises producing a signal having at least two voltage levels over time.

30. The method, as set forth in claim 25, wherein producing a multi-level voltage signal comprises producing a signal having at least four voltage levels over time.

31. The method, as set forth in claim 25, wherein producing a multi-level voltage signal comprises producing different voltage levels on different transmitter cell paths.

32. The method, as set forth in claim 25, wherein producing a multi-level voltage signal comprises producing multiple pulse cycles on the same transmitter cell path having different multi-level voltage waveforms within a single transmit cycle.

33. The method, as set forth in claim 25, wherein producing a multi-level voltage signal comprises producing a time-ratioed multi-level voltage signal.

* * * * *